United States Patent [19]

Callaway

[11] Patent Number: 5,233,978
[45] Date of Patent: Aug. 10, 1993

[54] NASAL OXYGEN MASK

[75] Inventor: James J. Callaway, Franklin, Tenn.

[73] Assignee: Medway, Franklin, Tenn.

[21] Appl. No.: 863,581

[22] Filed: Apr. 3, 1992

[51] Int. Cl.$^5$ .................. A62B 18/02; A61M 16/06
[52] U.S. Cl. ...................... 128/205.25; 128/206.28
[58] Field of Search ............... 128/204.18, 205.25, 128/204.26, 206.11, 206.12, 206.24, 206.28, 207.18, 206.21, 206.13, 206.14; D29/8, 9

[56] References Cited

U.S. PATENT DOCUMENTS

| | | | |
|---|---|---|---|
| D. 120,372 | 5/1940 | Boothby | D29/8 |
| D. 143,782 | 2/1946 | Yant | D29/8 |
| D. 203,912 | 2/1966 | DeAngelis | D29/8 |
| D. 262,322 | 12/1981 | Mizerak | D29/7 |
| D. 321,570 | 11/1991 | Blasdell | D29/8 |
| 1,050,621 | 1/1913 | De Ford | 128/206.28 |
| 1,139,850 | 5/1915 | Conkle | 128/206.28 |
| 1,206,045 | 11/1916 | Smith | 128/206.24 |
| 1,287,149 | 12/1918 | Walter | 128/206.28 X |
| 1,362,766 | 12/1920 | McGargill | 128/206.11 X |
| 1,562,302 | 11/1925 | Dean | 128/206.13 |
| 2,178,800 | 11/1939 | Lombard | 128/205.11 |
| 2,675,803 | 7/1951 | Kaslow | 128/205.25 X |
| 3,130,722 | 4/1964 | Dempsey | 128/206.28 |
| 3,315,672 | 4/1967 | Cunningham | 128/863 |
| 3,799,164 | 3/1974 | Rollins | 128/205.25 |
| 4,098,271 | 7/1978 | Maddock | 128/205.25 X |
| 4,201,205 | 5/1980 | Bartholomew | 128/205.25 |
| 4,216,769 | 8/1980 | Grimes | 128/207.13 |
| 4,231,363 | 11/1980 | Grimes | 128/205.25 |
| 4,354,488 | 10/1982 | Bartos | 128/205.25 |
| 4,377,162 | 3/1983 | Staver | 128/200.28 |
| 4,454,880 | 6/1984 | Muto et al. | 128/205.25 |
| 5,005,571 | 4/1991 | Dietz | 128/205.25 |
| 5,078,132 | 1/1992 | Braun | 128/206.12 |
| 5,143,061 | 9/1992 | Kaimer | 128/206.24 |

FOREIGN PATENT DOCUMENTS

| | | | |
|---|---|---|---|
| 1039144 | 9/1978 | Canada | 128/205.25 |
| 1085259 | 9/1980 | Canada | 128/205.25 |
| 38967 | 2/1924 | Norway | 128/205.25 |
| 874856 | 8/1961 | United Kingdom | 128/205.25 |
| 8200254 | 2/1982 | World Int. Prop. O. | 128/205.25 |

*Primary Examiner*—Edgar S. Burr
*Assistant Examiner*—Eric Raciti
*Attorney, Agent, or Firm*—Jacobson, Price, Holman & Stern

[57] ABSTRACT

A rearwardly and downwardly opening mask shell is provided for positioning about and over the nose and mouth face areas of a patient in a manner such that the mask shell seals rearwardly against the face of the patient and opens downwardly from the mouth area of the patient. Oxygen inlet means opens inwardly through opposite side portions of the mask shell aligned with the nostril area of the user, and therefore closely adjacent the mouth of the user, and flexible oxygen delivery tubes have discharge ends operatively connected with the oxygen inlet means and the tubes include opposite end portions for communication with an oxygen supply line and which are joined together through the utilization of a soft material connecting strip frictionally adjustable along the tubes such that the connecting strip may pass behind the neck of the user and the tubes may be used to retain the mask shell in position on the face of the user, the mask shell including an upper arched portion constructed of soft material for passing over the nose bridge area of the user and having malleable strip supported therefrom, which strip may be shaped for frictionally gripping the nose bridge area of the patient.

17 Claims, 2 Drawing Sheets

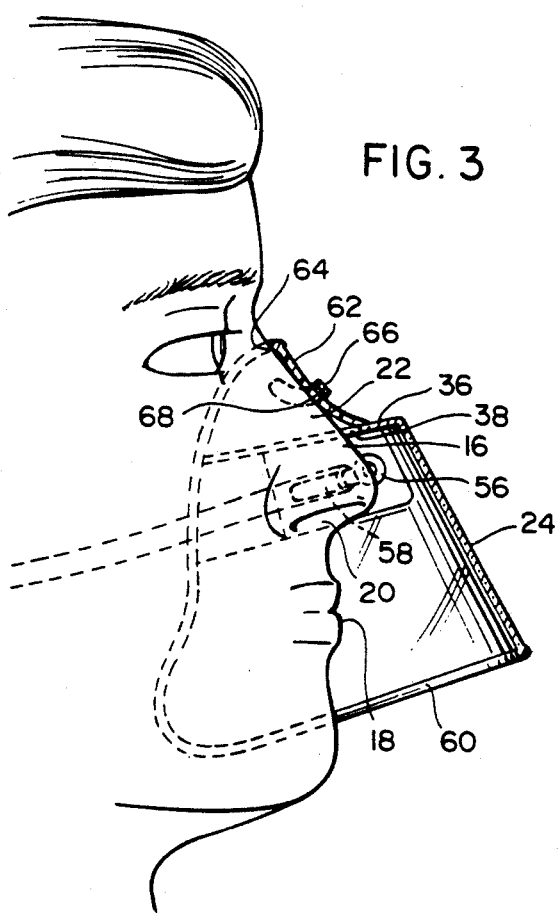
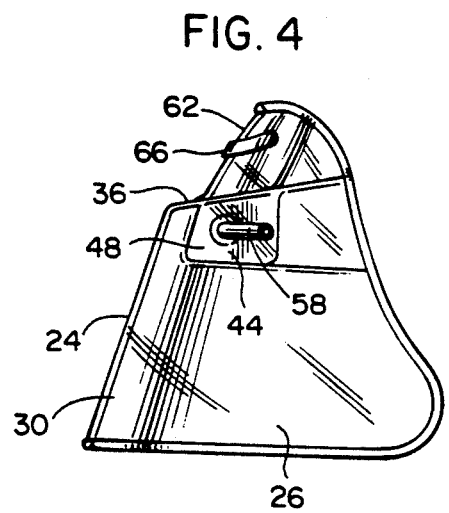
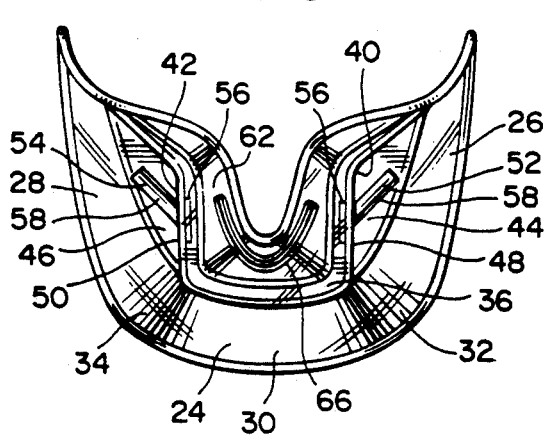
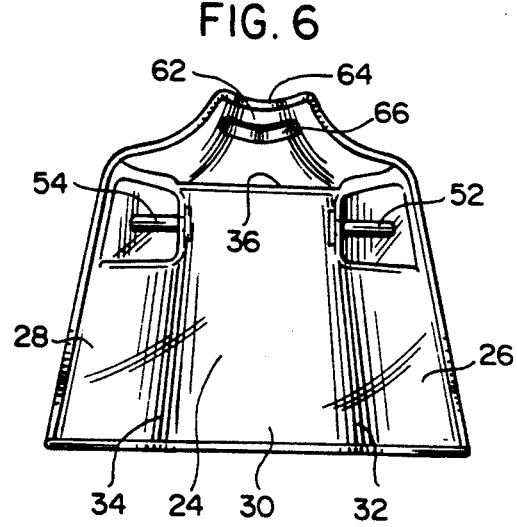

NASAL OXYGEN MASK

BACKGROUND OF THE INVENTION

1. Field Of The Invention

This invention relates to a rearwardly and downwardly opening mask to be worn over the nose and mouth areas of the face of a person and with opposite side portions of the mask having oxygen supply lines opening therethrough, the mask opening downwardly over the mouth area of the wearer and therefore comprising only a partial mask.

2. Description Of Related Art

Various different forms of full and partial masks heretofore have been designed for supplying an oxygen enriched or medicated atmosphere for breathing by a patient.

Examples of these previously known forms of masks, both and full and partial, are disclosed in U.S. Pat. Nos. 1,206,045, 2,178,800, 3,799,164, 4,201,205, 4,216,769, 4,231,363, 4,354,488, 4,377,162 and 4,454,880.

Some of these masks include opposite side oxygen supply inlet fittings and various structures are associated with these previously known masks for purpose of supporting the masks in operative position in relation to the face of the user or patient.

However, these previously known forms of masks do not include the overall combination of structural and operational features of the instant invention which together provide a mask which may be comfortably used by substantially all patients.

SUMMARY OF THE INVENTION

The partial mask of the instant invention has been specifically designed to provide a means for delivering moist oxygen to the nostril area of a patient independent of the use of a closed mask or nasal catheters.

Currently, oxygen is administered by either a face mask, a face tent, nasal catheters or, in the case of a critically ill patient, a mechanical ventilator. Not only does a ventilator serve as a source of oxygen, but it also mechanically ventilates the patient.

A face mask of the closed type adequately supplies oxygen to the patient, but has the disadvantage that it tightly encloses the nose and the mouth. Usually, a closed mask is held in place by an elastic band that passes over the ears of the patient and during periods of prolonged use, the elastic band may cause pressure soreness on the ears. In addition, a face mask of the closed type causes claustrophobia in some patients, especially if they are short of breath and such patients often attempt to remove the face mask.

Also, the oxygen supply line for a closed type face mask enters the mask from the front and hangs dependently from the center of the mask, this tending to pull the mask away from the face unless the elastic strap is firmly secured and is reasonably tensioned.

A face tent is similar to face mask but it is open on the top and is not as claustrophobic, but it is difficult for a patient to talk with either a face mask or a face tent. Also, both must be removed to expectorate, blow the nose or to drink liquids.

A nasal catheter avoids some of the problems of a closed mask and face tent, but has the disadvantage of being secured by placing the oxygen supply lines over the ears causing pressure irritation. Another disadvantage of nasal catheters is the marked drying effect from the stream of oxygen in the nostrils. Further, patients who are truly short of breath will mouth breathe and loose benefit of the oxygen being discharged into the nostrils.

The open mask of the instant invention obviates some of the above problems of both standard closed face mask or a face tent as well as nasal catheters. The open mask is provided with oxygen supply lines which approach from the rear and which may used to encircle the neck below the ears for the purpose of holding the mask in place by the elasticity of the oxygen supply lines which supply lines include portions thereof for disposition behind the neck of the patient secured together through the utilization of an adjustable connecting strip.

By this construction very little pressure is exerted on the supply lines as the light weight of the contoured open mask is sufficient to hold the mask in place, with the oxygen supply lines connected to the mask preventing the mask from falling forward. The mask is comfortable, not claustrophobic and the positioning of the oxygen supply lines around the neck eliminates the pressure discomfort of the elastic band previously needed to hold a face mask or tent in place.

Another advantage of the open mask of the instant invention is that humidified oxygen supplied thereto does not have the drying effect usually associated with oxygen supplied through nasal catheters and the open mask enables patients to receive full benefit of oxygen whether they mouth breathe or nasal breathe. Still further, by virtue of the open bottom of the mask, patients may talk easily, expectorate, blow their nose and drink with a straw.

The main object of this invention is to provide an oxygen mask which will be capable of supplying humidified oxygen to the nostril and mouth area of a patient in a manner such that the supplied oxygen has a minimal drying effect on nasal tissues.

Another object of this invention is to provide an oxygen mask of the open type and which will enable user patients to talk, expectorate, blow their nose and drink through a straw in a substantially unimpeded manner.

Another very important object of this invention is to provide an oxygen mask constructed in a manner such that it may be comfortably retained on the face of a user through the utilization of the associated oxygen supply lines and with the oxygen supply lines secured together behind the neck of the user and passing from the mask to the rear of the neck of the user along paths passing below the ears of the user.

Yet another very important object of this invention is to provide an oxygen mask of such configuration as to enable the mask to be constructed of shape retentive but flexible material with the thickness of the material being maintained at a minimum in order to reduce the weight thereof and the configuration of the mask itself serving to reinforce the material of which the mask is constructed in order that the mask may maintain its predetermined shape.

A further object of this invention is to provide a mask including a portion thereof for passage over the bridge of the nose of the user and including structure by which the nose bridge traversing portion of the mask may be lightly embracingly engaged with the nose bridge of the user.

A final object of this invention to be specifically enumerated herein is to provide an oxygen mask in accordance with the preceding objects and which will conform to conventional forms of manufacture, be of simple construction and easy to use so as to provide a device that will be economically feasible, long-lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 is an enlarged, central vertical sectional view of the mask portion of the assemblage in FIG. 1;

FIG. 4 is a left side elevational view of the mask;

FIG. 5 is a top plan view of the mask;

FIG. 6 is a front elevational view of the mask;

DESCRIPTION OF THE PREFERRED EMBODIMENT

Figure 1:
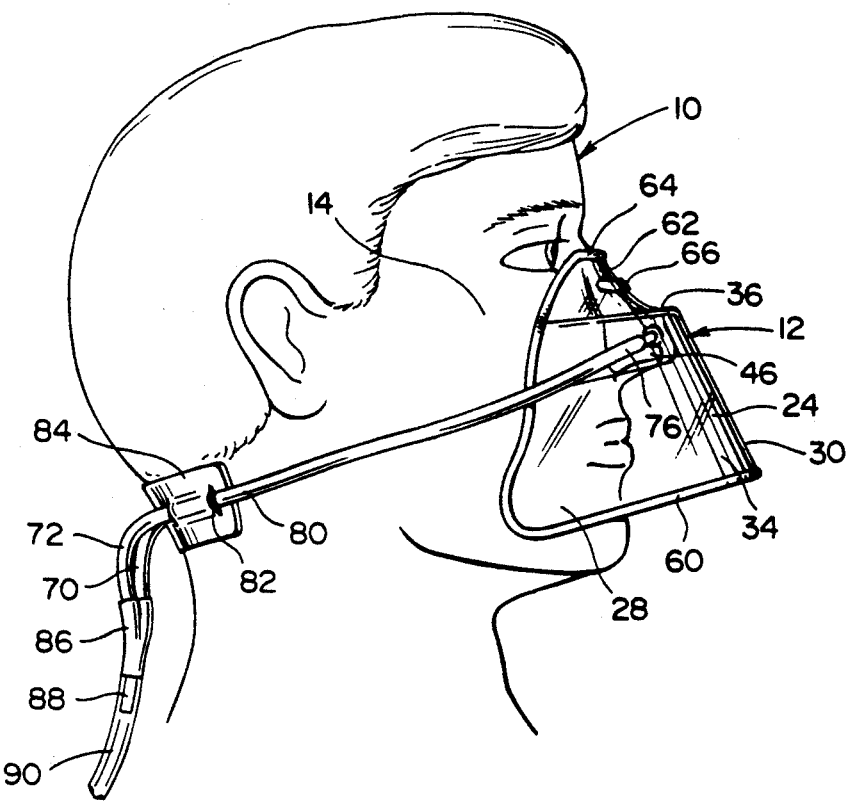
FIG. 1 is a right side elevational view of the head of a patient with the open mask of the instant invention operatively associated with the face of the patient and the oxygen supply lines operatively associated with the mask being utilized to retain the mask in position on the patients face.

Referring now more specifically to the drawings the numeral 10 generally designates a patients head with which a mask referred to in general by the reference numeral 12 and constructed in accordance with the present invention is operatively associated.

The head 10 includes a face area 14 including a nose 16 and a mouth 18, the nose 16 including opposite side nostril areas 20 and an upper bridge 22.

The mask 12 comprises a rearwardly and downwardly opening shell 24 constructed of stiff, but flexible material and including opposite side walls 26 and 28 and a front wall 30, the walls 26, 28 and 30 being downwardly divergent. The opposite side walls 26 and 28 and the front wall 30 are joined by integral, laterally curving and forwardly and downwardly inclined forward opposite side corner portions 32 and 34 which smoothly merge the forward extremities of the side walls 26 and 28 into the corresponding side portions of the front wall 30.

The front wall 30 and the opposite side walls 26 and 28 include upper margins which terminate upwardly in a generally horizontal shelf 36 having a rearwardly opening nose bridge receiving notch 38 formed therein spaced rearward and inward from the upper margins of the front wall 30 and the side walls 26 and 28, respectively.

The side walls 26 and 28 include indented portions 40 and 42 disposed immediately beneath the shelf 36 and defining upwardly and outwardly opening recesses 44 and 46 including forward, generally vertical, front-to-rear extending wall portions 48 and 50 having gas inlet fittings 52 and 54 secured therethrough. Each of the fittings 52 and 54 comprises a flanged tubular member whose flange 56 is abutted against and secured to the inner surfaces of the corresponding wall portion 46, 48 in any convenient manner and whose tubular member 58 extends through the corresponding wall portion and is inclined outwardly and rearwardly at generally 45 degrees.

The lower marginal edges of the front and side walls are rolled as at 60 as are the rear marginal edges of the side walls 26 and 28. In addition, the rearward marginal portions of the shelf 36 defining the notch 38 have the lower marginal portion of a rearwardly and downwardly opening shell section 62 secured thereto, the shell section 62 being constructed of flexible material with the upper rear extremity of the shell section 62 defining a horizontally rearwardly opening nose bridge receiving notch 64 spaced rearwardly above and aligned with the notch 38.

The shell section 62, between the upper rear extremity thereof and the lower marginal portions secured to the shell 36, includes an elongated transverse strip 66 of malleable material supported therefrom in any convenient manner such as by adhesive 68 and the strip 66 may be shaped, by pinching, for frictional gripping of the adjacent underlying portions of the shell section 62 with the underlying nose bridge 22.

Figure 2:
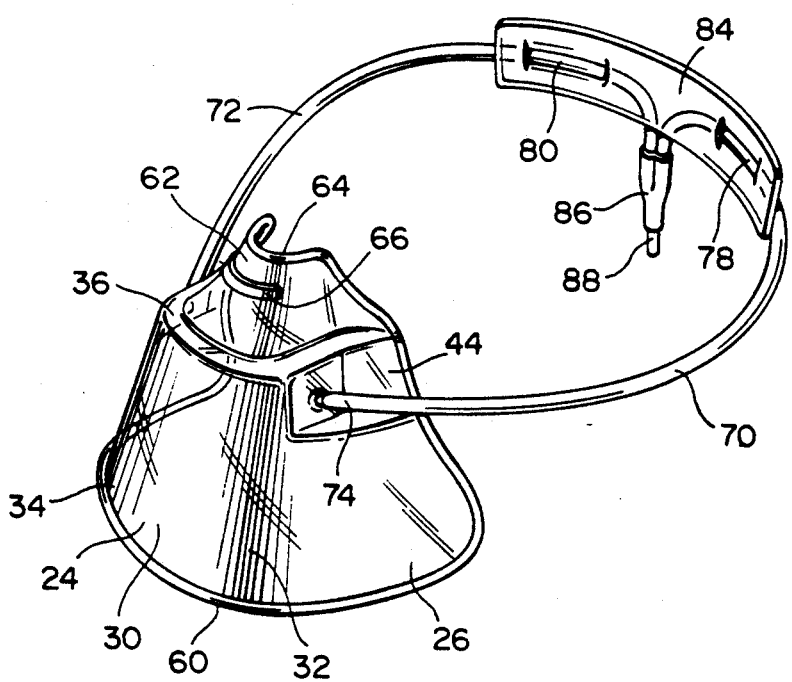
FIG. 2 is a perspective view of the assemblage of the invention illustrated in FIG. 1 as seen from a point forward of, spaced above and to the left of the assemblage.
Figure 7:
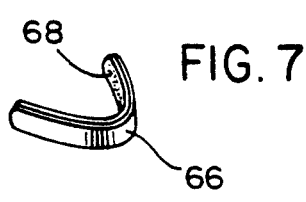
FIG. 7 is a enlarged perspective view of the malleable pinch strip secured to the upper forward portion of the mask and adapted to lightly clamp the nose bridge traversing portion of the mask to the associated patients nose bridge.
Figure 8:
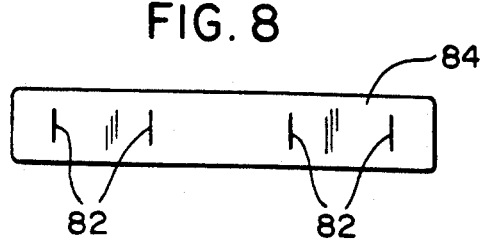
FIG. 8 is a plan view of the connecting strip to be adjustably secured between the supply ends of the oxygen supply lines associated with the mask.

As may best be seen from FIGS. 1 and 2 of the drawings, a pair of humidified oxygen delivery tubes 70 and 72 are provided and include a first set of corresponding discharge ends 74 and 76 and remote supply end portions 78 and 80. The discharge ends 74 and 76 are tightly telescoped over the tubular members 58 and the supply end portions 78 and 80 each are oppositely threaded through a pair of transverse slits 82 formed in and spaced along a corresponding end portion of a flexible connecting strap 84. The free ends of the supply end portions 78 and 80 are thereafter operatively connected with a Y-fitting 86 including an inlet nipple 88 to which an oxygen supply line 90 is connected.

As may be seen from FIG. 1, the connecting strip 84 (formed of a soft, flexible plastic) is frictionally retained in adjusted position along the end portions 78 and 80 to thereby adjust the loop formed by the connecting strip 84, the tubes 70 and 72 and the mask 12.

The size of this loop is adjusted in order to retain the mask 12 in proper position on the face of the head 10 in a manner which does not cause pressure upon the ears or any adverse pressure points insofar as the patient is concerned.

The additional frictional gripping of the mask 10 on the bridge 22 by the strip 66 is only minimal, but such additional minimal support of the very light weight shell 24 is sufficient to maintain the shell 24 stationary on the face 14. Further, by utilizing the tubes 70 and 72 in the manner illustrated in FIG. 1 in order to secure the shell 24 to the face 14 by attaching the end portions 78 and 80 of the tubes 70 and 72 together behind the neck of the patient, the shell 24 is very comfortably mounted upon the face 14. Further the shell 24 enables the patient to receive a proper supply of humidified oxygen, independent of whether the patient breathes through his nose or his mouth. Further, the shell 24 is not claustrophobic and allows the patient to expectorate, blow his nose and/or drink through a straw as well as to carry out a normal conversation.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A nasal oxygen mask comprising a shell constructed of stiff, but flexible material and including downwardly divergent front and opposite side walls joined by integral, forwardly and downwardly inclined forward opposite side corner portions said front and opposite walls having upper margins terminating in a generally horizontal shelf extending therebetween having a rearwardly opening nose bridge receiving notch formed therein, spaced rearward and inward and from said upper margins of said front wall and said side walls, respectively, said side walls including indented portions immediately beneath said shelf defining upwardly and outwardly opening recesses including forward, generally vertical front-to-rear extending wall portions including gas inlet fitting means opening through said wall portions for admitting gas into the interior of said shell from the exterior thereof, said shelf and those portions of said mask defining said recesses serving to stiffen said mask for shape retention thereof even though said material is flexible for comfort of the edges thereof adapted to seat against opposing patient skin portions.

2. The mask of claim 1 wherein the forward portions of said recesses open forwardly through said corner portions.

3. The mask of claim 1 wherein said gas inlet fitting means include tubular fittings secured through said wall portions.

4. The mask of claim 1 wherein the marginal portions of said shelf disposed about and rearward of said notch have the lower marginal portions of a rearwardly and downwardly opening shell section constructed of flexible material secured thereto and with the upper rear extremity of said shell section defining a horizontally rearwardly opening nose bridge receiving notch spaced rearwardly above and aligned with the first mentioned notch.

5. The mask of claim 4 wherein said shell section, between said upper rear extremity and said lower marginal portions, includes an elongated transverse strip of malleable material supported therefrom, which strip may be shaped, by pinching, for frictional gripping of the adjacent portions of said shell section with an underlying nose bridge portion.

6. A nasal oxygen mask comprising a shell constructed of stiff, but flexible material and including downwardly divergent front and opposite side walls joined by integral, forward opposite side corner portions said front and opposite side walls including upper margins defining a rearwardly opening nose bridge receiving notch, said side walls including indented portions immediately beneath said upper margins defining upwardly and outwardly opening recesses including forward, generally vertical front-to-rear extending wall portions including gas inlet fitting means opening through said wall portions for admitting gas into the interior of said shell from the exterior thereof.

7. The mask of claim 6 wherein said fitting means include flanged tubular members whose flanges are abutted against and secured to the inner surfaces of said wall portions with said tubular members extending through said wall portions and inclined generally 45 degrees relative thereto, said tubular members including inlet ends opening endwise outwardly of said recesses in oppositely rearwardly and outwardly directed directions.

8. The mask of claim 7 including a pair of elongated, flexible oxygen delivery tubes having a first set of discharge ends sealingly telescoped over said inlet ends, said delivery tubes extending rearwardly and outwardly of said opposite side walls and including supply end portions opposite said discharge ends, an elongated flexible strip including opposite ends portions each including a pair of closed ended transverse slits formed therein and laterally spaced apart longitudinally thereof, said supply end portions each including being oppositely tightly threaded through a corresponding pair of said slits with said strips serving to join said supply end portions by forming a flexible bridge therebetween frictionally adjustable along said supply end portions.

9. A nasal oxygen mask comprising a shell constructed of stiff, but flexible material and including downwardly divergent front and opposite side walls joined be integral, forward opposite side corner portions said front and opposite side walls including upper margins defining a rearwardly opening nose bridge receiving notch, a rearwardly opening shell section constructed of flexible material and including a lower marginal portion secured to said upper margins, said shell section including an upper rear extremity defining a horizontally rearwardly opening nose bridge receiving notch spaced rearwardly above and aligned with the first mentioned notch.

10. The mask of claim 9 wherein said shell section, between said upper rear extremity and said lower marginal portion, includes an elongated transverse strip of malleable material supported therefrom, which strip may be shaped, by pinching, for frictional gripping of the adjacent portions of said shell section with an underlying nose bridge portion.

11. The mask of claim 1 wherein said fitting means include flange tubular members whose flanges are abutted against and secured to the inner surfaces of said wall portions with said tubular members extending through said wall portions and inclined generally 45 degrees relative thereto, said tubular members including inlet ends opening endwise outwardly of said recesses in oppositely rearwardly and outwardly directed directions.

12. The mask of claim 11 including a pair of elongated, flexible oxygen delivery tubes having a first set of discharge ends sealingly telescoped over said inlet ends, said delivery tubes extending rearwardly and outwardly of said opposite side walls and including supply end portions opposite said discharge ends, an elongated flexible strip including opposite ends portions each including a pair of closed ended transverse slits formed therein and laterally spaced apart longitudinally thereof, said supply end portions each including being oppositely tightly threaded through a corresponding pair of said slits with said strips serving to join said supply end portions by forming a flexible bridge therebetween frictionally adjustable along said supply end portions.

13. The mask of claim 12 wherein the forward portions of said recesses open forwardly through said corner portions.

14. The mask of claim 13 wherein said gas inlet fitting means include tubular fittings secured through said wall portions.

15. The mask of claim 14 wherein the marginal portions of said shelf disposed about and rearward of said notch have the lower marginal portions of a rearwardly and downwardly opening shell section constructed of flexible material secured thereto and with the upper rear extremity of said shell section defining a horizontally rearwardly opening nose bridge receiving notch spaced rearwardly above and aligned with the first mentioned notch.

16. The mask of claim 15 wherein said shell section, between said upper rear extremity and said lower marginal portions, includes an elongated transverse strip of malleable material supported therefrom, which strip may be shaped, by pinching, for frictional gripping of the adjacent portions of said shell section with an underlying nose bridge portion.

17. The mask of claim 1 wherein said opposite side corner portions are laterally curved and smoothly merge, together, adjacent portions of said front and side walls.

* * * * *